United States Patent [19]
Amselem

[11] Patent Number: 5,989,583
[45] Date of Patent: *Nov. 23, 1999

[54] SOLID LIPID COMPOSITIONS OF LIPOPHILIC COMPOUNDS FOR ENHANCED ORAL BIOAVAILABILITY

[75] Inventor: Shimon Amselem, Rehovot, Israel

[73] Assignee: Pharmos Ltd., Rehovot, Israel

[ * ] Notice: This patent issued on a continued prosecution application filed under 37 CFR 1.53(d), and is subject to the twenty year patent term provisions of 35 U.S.C. 154(a)(2).

[21] Appl. No.: 08/833,075

[22] Filed: Apr. 2, 1997

[30] Foreign Application Priority Data

Apr. 2, 1996 [IL] Israel ................................. 117773

[51] Int. Cl.$^6$ ............................... A61K 9/14; A61K 9/20; A61K 9/48
[52] U.S. Cl. .................. 424/439; 424/456; 424/464; 424/465; 424/452; 424/450; 424/489; 426/590; 514/169; 514/724; 514/728; 514/962
[58] Field of Search ..................... 424/450, 452, 424/489, 456, 464, 465, 439; 426/590; 514/169, 962, 724, 728; 264/4.1, 4.3

[56] References Cited

U.S. PATENT DOCUMENTS

| | | | |
|---|---|---|---|
| 4,687,782 | 8/1987 | Brantman | 514/561 |
| 5,179,122 | 1/1993 | Greene et al. | 514/458 |
| 5,480,865 | 1/1996 | Kingham | 514/2 |
| 5,665,379 | 9/1997 | Herslof | 424/450 |

FOREIGN PATENT DOCUMENTS

| | | |
|---|---|---|
| 0084169 | 12/1982 | European Pat. Off. . |
| 0084169 | 7/1983 | European Pat. Off. . |
| 2050287 | 1/1983 | United Kingdom . |
| 2050287 | 1/1991 | United Kingdom . |

*Primary Examiner*—Gollamudi S. Kishore
*Attorney, Agent, or Firm*—Pennie & Edmonds LLP

[57] ABSTRACT

Lipophilic substances of poor oral bioavailability are mixed with at least one solid fat and phospholipid to obtain a dried solid composition suitable as an oral dosage form. The solid lipid compositions are exemplified for food additives or dietary supplements such as Coenzyme Q10 and for pharmaceuticals such as dexanabinol. The Coenzyme Q10-dry lipid mixtures shows improved drug release in vitro and enhanced oral bioavailability in vivo compared to a commercial CoQ10 formulation. The dexanabinol-dry lipid mixture similarly shows greatly enhanced oral bioavailability compared to known formulations.

20 Claims, 4 Drawing Sheets

SOLID LIPID COMPOSITIONS OF LIPOPHILIC COMPOUNDS FOR ENHANCED ORAL BIOAVAILABILITY

FIELD OF THE INVENTION

The present invention concerns compositions comprising dry lipid mixtures of lipophilic compounds and to methods for the preparation and use of these compositions.

BACKGROUND OF THE INVENTION

Lipophilic substances possessing low water solubility often have poor oral bioavailability. These compounds, being hydrophobic by nature, show wetting difficulties and poor dissolution. These properties obviously represent a rate-limiting step in their absorption from solid oral dosage forms and, in turn, cause a subsequent reduction in their bioavailability.

To address the foregoing issues, these lipophilic substances are usually administered in the form of liquid preparations dissolved in edible oils or formulated in oil-in-water emulsions or microemulsions. Even in these formulations, however, the oral bioavailability of many of them is still very low. Thus, even today, there remains an unresolved need to provide safe and useful formulations that provide enhanced oral bioavailability for such substances.

Coenzyme Q10 (CoQ10), chemically named as 2,3-dimethoxy-5-methyl-6-decaprenyl-1,4-benzoquinone and also known by the names Ubiquinone, and Vitamin Q, is classified as a fat-soluble quinone, a naturally occurring coenzyme. It has been identified as an essential component of the mitochondrial respiratory chain and, thus, a necessary part of a cell's energy production. More particularly, it constitutes a redox-link between flavoproteins and cytochromes and acts as an electron shuttle controlling the efficiency of oxidative phosphorylation. Without ubiquinone, cells cannot produce the energy necessary for all the body's many activities.

The name ubiquinone is derived from the word ubiquitous and, indeed, ubiquinone is a naturally occurring substance in almost every cell. Typically, the substance is found in small organelles called mitochondria, which act as the cell's energy factories. Mitochondria convert energy from nutritional substances to energy that is then used for all the body's activities.

CoQ10 has been previously identified as an antioxidant with potential use as a dietary supplement to protect against age-related degeneration and as an adjuvant vitamin to prevent or treat many disease states.

Supplementary Coenzyme Q10 has also reportedly shown beneficial influences in the following systems, conditions or diseases: periodontal disease, certain blood circulation diseases, impaired memory, fatigue, irregular heartbeat, high blood pressure, an immune system impairment, and the aging process. Moreover, Coenzyme Q10 has been reported to be capable of improving one's performance in sports.

Although known for many years to protect biological membranes against oxidation, CoQ10 has recaptured interest as a natural, powerful lipid-soluble antioxidant which acts as a membrane stabilizing agent. It, therefore, avoids lipid peroxidation and regulates lipid fluidity—probably by removing free radicals (Beyer R.E., The participation of coenzyme-Q in free radical production and anti-oxidation, Free Rad. Biol. Med., 8, 545–565, 1990). It is assumed that part of the substance's beneficial effect on heart disease and periodontal disease is due to its ability to neutralize free radicals in the affected tissue. Heart patients have been shown to have low levels of coenzyme Q10, and the liver's ability to produce coenzyme Q10 is debilitated as one becomes older.

The role of Coenzyme Q10 in the production of energy has also been demonstrated in the treatment of cardiomyopathy, a condition in which the actual muscle tissues of the heart are weakened, making it difficult for the heart to pump blood around the body effectively. Mortensen et al., have published results of long term coenzyme Q10 treatment for cardiomypathic patients (in Drugs under Experimental and Clinical Research, Vol 11, No. 8, pp. 581, 1985). Among 40 patients with severe heart failure, 69% showed improvements in their condition when treated with coenzyme Q10. Coenzyme Q10's beneficial affect on the heart's ability to pump is apparently due to its ability to increase the creation of the energy substance ATP in the heart. The strengthened heart is then better able to pump blood around the body.

The efficacy of coenzyme Q10 as an adjuvant therapy in heart diseases in a multicenter study has also been reported (Lampertico M., and Comis S., Italian multicenter study on the efficacy and safety of coenzyme Q10 as adjuvant therapy in heart failure, Clin. Investig., 71, S129–133, 1993). The most prevalent of all heart diseases is arteriosclerosis, a hardening of the heart's blood vessels and a condition often complicated by coronary thrombosis. Coenzyme Q10 has also been proposed to help fight this disease and strengthen the pumping action in cases where a lack of oxygen has debilitated the heart's muscle tissue.

Scientists have also investigated the effects of a dietary supplement of coenzyme Q10 on periodontitis. For example, in one study, the tissue samples of over 120 dental patients with periodontal disease were examined and were found to have a marked deficiency of CoQ10 (Wilkinson et al., Biomedical and Clinical Aspects of Coenzyme Q, pp 103–108, Elsevier/North Holland Biomedical Press, 1980). When the patients were treated with supplements containing CoQ10, the progress of the disease was not only stopped, but accelerated tissue healing was initiated as well. Such evidence appears to suggest that the spread of the disease can often be slowed down and, indeed, even stopped by coenzyme Q10. Coenzyme Q10 apparently facilitates the healing process by increasing the production of energy in the infected tissue. Coenzyme Q10 may also provide such benefits based on its antioxidant roperties which neutralize the harmful effects of free radicals.

Coenzyme Q10 has also been shown to protect cultured cerebellar neurons against age-related and excitotoxin-induced degeneration (Favit A., Nicoletti F., Scapagnini U., and Canonico P. L., Ubiquinone protects cultured neurons against spontaneous and excitotoxin-induced degeneration, J. Cerebral Blood Flow and Metab. 12, 638–645, 1992).

The recommended daily allowance for coenzyme Q10 has not been determined. Most experts agree, however, that the daily requirement lies somewhere between 30 and 60 milligrams. When treating illnesses, dosages of 100 to 300 milligrams are commonly used.

CoQ10 is a very lipophilic compound and practically insoluble in water due to its long side chain of 10 isoprenoid units. The oral bioavailability of CoQ10 is, therefore, generally very low and was found to be related to the dissolution rate of the formulation. The formulation of this substance in a suitable form affording convenient and efficient oral bioavailability is, therefore, a very desirable goal.

Emulsions and microemulsions have been shown to be advantageous vehicles for the oral delivery of lipophilic drugs, resulting in improved oral bioavailability of water-insoluble compounds (Tarr B. D. and Yalkowsky S. H., Enhanced intestinal absorption of cyclosporine in rats through the reduction of emulsion droplet size, Pharmac. Res. 6,40–43, 1989; Charman S. A., Charman W. N., Rogge M. C., Wilson T. D., Dutko F. J., and Pouton C. W., Self-dry lipid mixtures drug delivery systems: formulation and biopharmaceutic evaluation of an investigational lipophilic compound, Pharmac. Res. 9, 87–93, 1992).

Formulations of Coenzyme Q10 using lipids, in the form of emulsions, liposomes, microparticles and nanoparticles, have previously been disclosed. These known lipid formulations comprise particles dispersed in an aqueous medium, and are suitable for various routes of administration, including, primarily, intravenous administration, as disclosed in: WO 95/05164, which discloses microparticles and nanoparticles in aqueous suspension; U.S. Pat. No. 4,824, 669, which discloses fatty emulsions; U.S. Pat. No. 4636381, which discloses liposomes; and U.S. Pat. No. 4,483,873, which discloses aqueous dispersions or solutions.

Other lipid formulations of Coenzyme Q10 have been disclosed for improved oral bioavailability, as in: WO 86/04503, which utilizes a high percentage of a synthetic surfactant agent together with a fat or with polyethylene glycol; JP 63188623, which discloses Coenzyme Q10 with middle chain fatty acid monoglycerine esters, and optional plant oil; and U.S. Pat. No. 4,684,520 which provides mixtures of Coenzyme Q10 with phospholipids.

Cannabinoids are one example of a family of lipophilic substances having very poor water solubility. Cannabinoids such as $\Delta^1$-tetrahydrocannabinol ($\Delta^1$-THC), $\Delta^6$-tetrahydrocannabinol ($\Delta^6$-THC), $\Delta^9$-tetrahydrocannabinol ($\Delta^9$-THC), cannabinol, cannabidiol, and their metabolites, are highly hydrophobic lipid soluble compounds and can be dissolved in aqueous solutions only in the range of a few micrograms/ml or less, depending upon conditions (Garret and Hunt, J. Pharm. Sci., 63:1056–1064, 1974).

In general, the systemic availability of cannabinoids after oral administration is low and mean estimates of the human bioavailability of tetrahydrocannabinol (THC) following oral ingestion range from 6 to 12% depending on the vehicle used. For example, the maximal plasma levels after oral dosing of 20 mg THC in a sesame oil formulation are around 10 ng/ml (Wall et al., Clin. Pharmacol. Ther. 34:352–363, 1983).

Dexanabinol, (+)-(3S,4S)-7-hydroxy-,$\Delta^6$-tetra hydrocannabinol-1,1-dimetylheptyl,(also denoted HU-211), is disclosed in U.S. Pat. Nos. 4,876,276 and 5,521,215, as a synthetic non-psychoactive cannabinoid with novel neuroprotective activity in the multiple-action treatment of brain damage associated with stroke, head trauma, and cardiac arrest. The chemical structure of dexanabinol, (+)-(3S, 4S) -7-hydroxy-$\Delta^6$-tetra hydrocannabinol-1,1-dimetylheptyl, is shown in Scheme 1.

Scheme 1

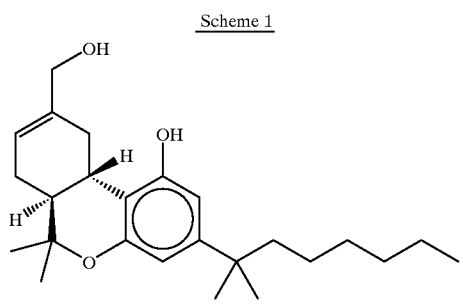

Dexanabinol is a very lipophilic compound which is practically insoluble in water (less than 50 $\mu$g/ml) and, like other lipophilic drugs, exhibits poor oral bioavailability.

SUMMARY OF THE INVENTION

This invention is directed to dry solid lipid compositions useful for the oral delivery of lipophilic substances, and to methods for preparing and using such compositions.

The dry solid lipid mixtures of the present invention include a first component of a lipophilic substance in an amount sufficient to provide a therapeutic effect when administered to a mammal; a second component of a lipid comprising at least one solid fat; and a third component of at least one phospholipid, wherein the second and third components are present in an amount sufficient to increase the oral availability of the lipophilic substance when administered to the mammal.

According to preferred embodiments of the present invention, these dry solid lipid mixtures advantageously include one or more of an antioxidant, a cryoprotectant or a free-flow imparting agent.

The dry solid lipid mixtures of the present invention have shown unexpectedly high drug-loading efficiency and enhanced oral bioavailability for the lipophilic compounds.

The present invention further relates to methods for producing such dry solid lipid mixture compositions by dissolving the lipophilic substance together with lipid components comprising at least one solid fat and at least one phospholipid in a suitable organic solvent;

evaporating the solvent to dryness;

hydrating the dry solid lipid mixture with an aqueous phase, with mechanical shaking, to obtain a lipid dispersion in water;

homogenizing the resultant lipid dispersion, such as by high-pressure homogenization, to reduce the particle size to the submicron range; and drying the submicron dispersion.

According to another embodiment, the dry solid lipid mixtures according to the present invention may be prepared by directly drying the lipid mixture that is dissolved in the organic solvent. For example, the solid lipid mixture formulations can be spray dried or freeze-dried to obtain dry compositions suitable for the preparation of solid-dosage forms, such as hard gelatin capsules or tablets. These solid dosage forms may further comprise cryoprotectants, antioxidants, free flowing imparting agents, surface active materials and/or emulsifiers.

These lipid compositions are advantageous for the oral delivery of lipophilic compounds of dietary supplements or food additives, such as the dietary nutrient supplement CoQ10, or for any appropriate lipophilic drug or compound with very low water solubility, such as dexanabinol.

DETAILED DESCRIPTION OF THE INVENTION

Figure 1:
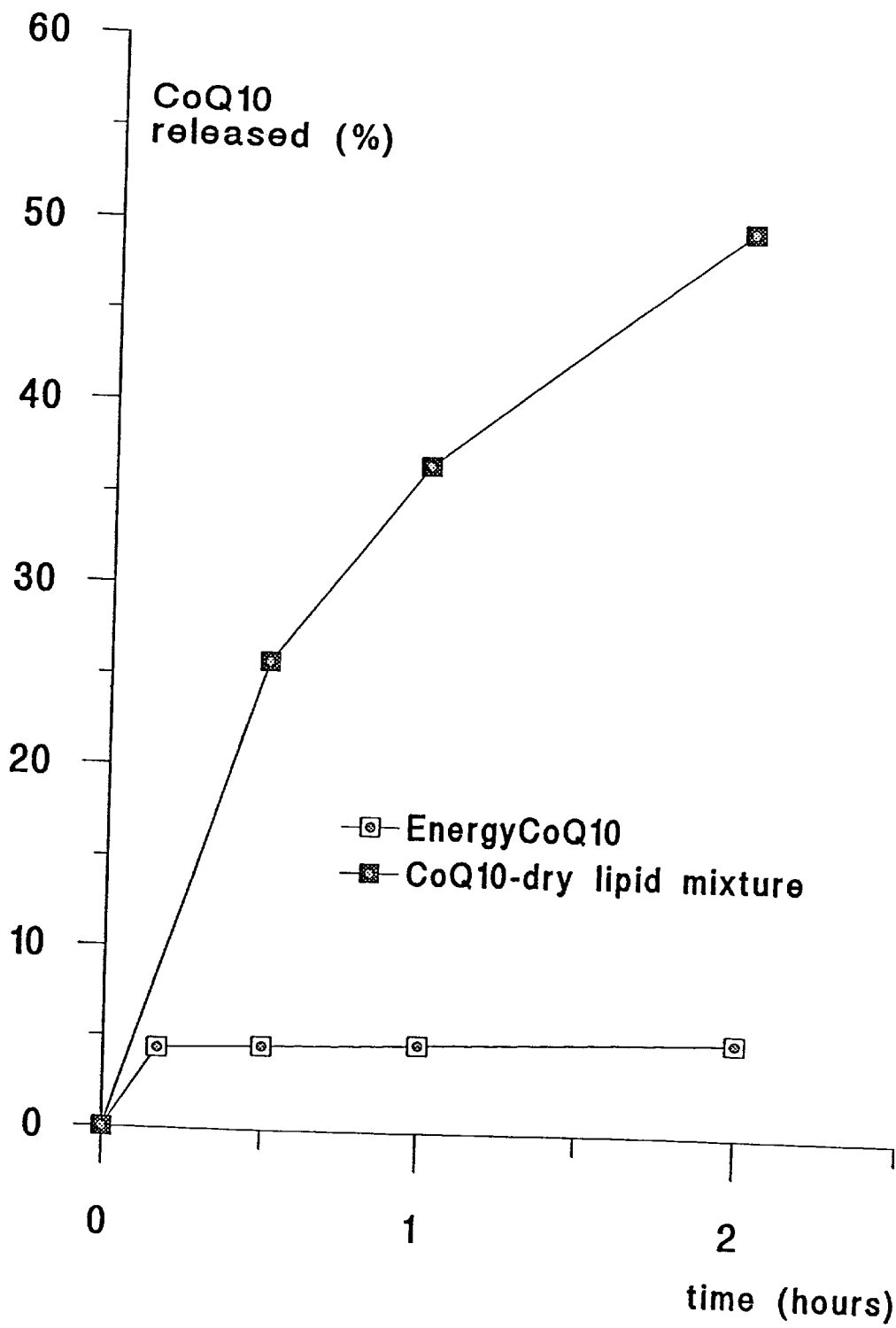
FIG. 1 shows the in vitro release of CoQ10 in simulated gastric fluid from commercial ENERGYCO® CoQ10 gelatin capsules (Herbamed-Assutech Ltd., Rehovot, Israel) and from a CoQ10-dry lipid mixture prepared as described in Examples 1–5 (Table 1 and 2)and packed in gelatin capsules.

This invention is directed to dry solid lipid compositions for the oral delivery of lipophilic substances, and to methods for preparing and using such compositions.

The dry solid lipid mixtures of the present invention are composed of three primary ingredients: a lipophilic substance, a lipid or lipid mixture comprising at least one solid fat, and one or more phospholipids. Advantageously, the dry lipid mixtures of the present invention, may further comprise an antioxidant, a cryoprotectant or a free-flow imparting agent.

Any of a wide variety of lipophilic substances can be utilized in these mixtures. Examples include lipophilic drugs, vitamins, and hormones. These lipophilic substances include steroids, steroid antagonists, non-steroidal anti-inflammatory agents, antifungal agents, antibacterial agents, antiviral agents, anticancer agents, anti-hypertensives, anti-oxidants, anti-epileptic agents and antidepressants among many others. Additional examples of lipophilic drugs with very poor water solubility and low oral bioavailability which could benefit from oral dosage forms are the neurohormone melatonin, the antifungal agent amphotericin B, the anticancer drug etoposide, as well as tamoxifen and its analogs. More specific compounds include cannabinoids, as exemplified by dexanabinol, and vitamins, enzymes or coenzymes, as exemplified by CoQ10. Preferred lipophilic substances are those which have a water solubility of <200 µg/ml in water at room temperature (25° C.), and more preferably <50 µg/ml.

The content of the lipophilic substance in the final dry solid lipid mixture may range from about 0.01–50% of the total solid weight of the mixture, more preferably in the range of about 5–40% of the total solid weight of the mixture, and still more preferably about 7–30% of the total solid weight of the mixture.

In the following description and claims, the term "solid fat" denotes any lipid or mixture of lipids, provided that the melting characteristics of the lipid or mixture are such that they exhibit a solid or liquid crystal phase at about 25° C.

Triglycerides which are solid at room temperature are the preferred fats for the preparation of the lipid mixture. The solid triglycerides may be composed of a single pure triglyceride, usually available as a synthetic triglyceride, or may be a mixture of several triglycerides. Fats isolated from natural sources usually are available only as mixtures of triglycerides. Such natural mixtures are suitable for the preparation of dry lipid mixtures, provided that the melting characteristics of the mixture are such that they exhibit a solid or liquid crystal phase at about 25° C.

Examples of solid fats suitable for the preparation of dry lipid mixtures of the present invention are triglycerides composed of natural, even-numbered and unbranched fatty acids with chain lengths in the $C_{10}$–$C_{18}$ range, or microcrystalline glycerol triesters of saturated, even-numbered and unbranched fatty acids of natural origin such as tricaprin, trilaurin, trimyristin, tripalmitin, and tristearin.

The content of solid triglycerides in the final dry lipid mixture is in the range of about 20–75% of the total solid weight of the mixture, more preferably in the range of about 25–50% of the total solid weight of the mixture, and still more preferably in the range of about 30–45% of the total solid weight of the mixture.

The preferred phospholipids which constitute the third component of the dry lipid mixture of the present invention are natural phospholipids, such as: soybean lecithin, egg lecithin, phosphatidylglycerol, phosphatidylinositol, phosphatidylethanolamine, phosphatidic acid, sphingomyelin, diphosphatidylglycerol, phosphatidylserine, phosphatidylcholine, cardiolipin, etc.; synthetic phospholipids, such as dimyristoylphosphatidylcholine, dimyristoyl-phosphatidylglycerol, distearoylphosphatidylglycerol, dipalmitoylphosphatidylcholine, etc.; and hydrogenated or partially hydrogenated lecithins and phospholipids.

The phospholipid component may be either saturated or unsaturated, and may have a gel to fluid phase transition temperature either above or below about 25° C. Egg or soy phosphatidylcholines (egg or soy PC) are examples of phospholipids with transition temperatures well below room temperature. Dimyristoyl phosphatidylcholine (DMPC) has a transition temperature slightly below room temperature. Dipalmitoyl and distearoyl phosphatidylcholines (DPPC and DSPC) are examples of phospholipids with transition temperatures well above room temperature, and, in fact, even above physiological temperature (about 37° C.). Acceptable dry lipid mixtures may be made with these and many other phospholipids.

Dry lipid mixtures may be prepared with molar ratios of phospholipid to total lipid in the range of about 0.1 to 0.75 (about 10 to 75 mol %), more usually about 0.1 to 0.5 (about 10 to 50 mol %). The molar ratio of phospholipid to total lipid typically may be in the range of about 0.1:1 to 2:1, usually about 0.1:1 to 1:1, often about 0.2:1 to 0.9:1, frequently about 0.2:1 to 0.8:1, and commonly about 0.25:1 to 0.6:1.

On a weight basis, the ratio of phospholipid to total lipid is at least 0.1:1 to 2:1, and preferably 0.2:1 to 1:1. This ratio usually falls in the range of about 0.4:1 to 1.5:1, and frequently about 0.5:1 to 1.25:1.

The content of phospholipids in the final dry solid lipid mixture is commonly in the range of about 2–40% of the total solid weight of the mixture, more preferably about 5–35%, and still more preferably about 10–30% of total solid weight of the mixture.

The dry solid lipid mixture of this invention optionally may contain one or more additional antioxidants. Antioxidants lessen the formation of oxidative degradation products, such as peroxides, from the unsaturated lipids, or other components. A non-limiting example of such a preferred antioxidant is α-tocopherol, or its derivatives (such as tocopherol succinate), which are members of the Vitamin E family. Many other antioxidants which are known in the art as safe for human consumption may be used, such as butylated hydroxytoluene (BHT). The content of the antioxidant in the final dry solid lipid mixture is commonly in the range of about 0.01–5% of the total solid weight of the mixture, more preferably about 0.05–3% of the total solid weight of the mixture, and still more preferably about 0.1–1% of the total solid weight of the mixture.

Dry solid lipid mixtures may advantageously further comprise a cryoprotectant material as known in the art, such as a sugar or an amino compound, to preserve the formulation during freeze-drying or spray-drying processes used in the preparation of the dry solid CoQ10-lipid mixtures.

Preferred cryoprotectants include glucose, sucrose, lactose, maltose, and trehalose; polysaccharides, such as dextrose, dextrins, and cyclodextrins; and nonnatural polymers, such as polyvinylpyrrolidone (PVP). Other types of cryoprotectants may also be used, including amino acids, as disclosed in U.S . Pat. No. 5,472,706. The preferred range of cryoprotectant to total solids in the dry solid lipid mixtures is about 0.1% up to 50% (w/w). A final weight % in the range of about 20–40% is commonly used in the preparation of dry solid lipid mixtures.

The dry solid lipid mixtures of the present invention may further comprise any suitable nontoxic carrier or diluent powder, known in the art, to serve as a free-flow imparting agent. Common examples of such additives are silicon dioxide, starch, lactose, sucrose, sorbitol, talc, stearic acid, magnesium stearate, and dicalcium phosphate. When the mixture is formulated into a tablet or pill, the tablet or pill can be coated or otherwise compounded with pharmaceutically acceptable materials known in the art to provide a dosage form affording prolonged action or sustained release. The dry solid lipid mixtures may also be prepared in gelatin capsules.

According to a preferred embodiment the dry solid lipid mixtures are further mixed with fumed silica such as CAB-0-SIL® (Cabot Corp., Ill., US), which is fumed silicon dioxide. This compound is a powdery material with extremely small particle size and enormous surface area. Fumed silica can act as a dry lubricant, promoting the free flow of the powdery mixture and preventing the mixture from caking or lumping. The free-flow, anti-caking and anti-clogging characteristics of this compound are the result of several actions. For example, the submicroscopic size of the silica aggregates permits them to move easily between the larger particles of the other dry agents, and, in most cases, fumed silica probably forms a coating on the powder particles. The fumed silica layer also decreases bulk tensile strength and shear strength, while neutralizing the electrostatic charge on the particles.

After blending with the other powders, fumed silica adsorbs some or all the moisture which may be present in or on the product particles. The fumed silica aggregates, therefore, prevent other particles from contacting each other and, in turn, from forming the nuclei that would otherwise lead to the formation of larger lumps and cakes. This spacing and lubricating action helps to keep materials moving through apertures, such as process equipment valves, spray heads, storage bin openings, bag and drum spouts and aerosol nozzle orifices.

Most powdered materials can be kept free flowing by adding a concentration of fumed silica in the final product range of about 0.5–50% (total solid weight). The optimum concentration can be determined by working up or down in small steps. The more preferred weight percent of fumed silica in the final product will be in the range of about 1–40% (total solid weight). Even powders which have already become caked can usually be rendered free flowing by blending them in fumed silica (about 2% of the total solid weight, or less). The tremendous surface area of fumed silica is the reason very small amounts can provide effective action.

Products which cannot be processed beyond a sticky or tacky powder can be made free flowing by adding the proper level of fumed silica as a final finishing step. Fumed silica can also be used to promote free flow in spray-dried or freeze-dried products.

In some cases it can be introduced into the original emulsion, suspension or solution, or blended in later. Fumed silica has also been used to coat powdered and pelletized products to prevent them from caking later.

The content of silicon dioxide in the final dry solid lipid mixture is commonly in the range of about 5–40% of the total solid weight of the mixture.

The dry drug-lipid mixtures of the present invention may be prepared by different methods as described in the following non-limiting examples appearing below.

EXAMPLES

Example 1

Preparation of Dry CoQ10-Lipid Mixture by Freeze-Drying from an Aqueous Dispersion This example illustrates the preparation of a dry CoQ10-lipid mixture by freeze-drying from an aqueous dispersion. The final dry composition of the formulation is described in table 1.

TABLE 1

| Composition of dry CoQ10-lipid mixture prepared by freeze-drying | |
|---|---|
| AGENTS | % w/w |
| Coenzyme Q10 | 11.7 |
| Tricaprin | 33.7 |
| Lecithin | 16.8 |
| Tocopherol succinate | 0.4 |
| Sucrose | 23.9 |
| Silicon dioxide | 13.5 |

Ubiquinone (Coenzyme Q10) was obtained from Global Marketing Associates, Inc. (San Francisco, Calif.). D-α tocopherol succinate was purchased from Merck (Germany). Lecithin was from Lipoid KG (Germany). Tricaprin was obtained from Hulls (Germany). CAB-O-SIL was from Cabot Corp. COQ10 was dissolved together with the lipid agents (phospholipids, tocopherol succinate and solid triglycerides) in dichloromethane. The solvent was evaporated until complete dryness, and the dry solid lipid mixture was then hydrated with the aqueous phase by mechanical shaking. The resultant lipid dispersion was consequently homogenized by high-pressure homogenization (800 bar) using an EMULSIFLEX™ C-30 high pressure homogenizer (Avestin Inc., Canada) to reduce the particle size to the submicron range. To the resultant dry CoQ10-lipid preparation, the cryoprotectant, sucrose (from a 40% w/w water solution), and the free-flowing imparting agent, CAB-0-SIL fumed silicon dioxide (from a 5% w/w suspension in water), were added and the formulation was then freeze-dried using a Christ lyophilizer (Germany). The weight ratio of phospholipids to total lipids was 0.33:1.

the final CoQ10 dry-lipid powder was filled into hard gelatin capsules.

Example 2

Preparation of Dry CoQ10-Lipid Mixture by Direct Freeze-Drying from a Tert-Butanol Solution This example illustrates the preparation of dry CoQ10-lipid mixtures by direct freeze-drying from tertiary-butanol solutions. The final ranges of dry composition of the formulations a re as described in Table 2.

TABLE 2

Composition of dry CoQ10-lipid mixture prepared by direct freeze-drying from a tert-butanol solution

| AGENTS | % w/w |
|---|---|
| Coenzyme Q10 | 9–19 |
| Tricaprin | 37–41 |
| Lecithin | 18–21 |
| Tocopherol succinate | 0.4–0.6 |
| Polyvinylpyrrolidone | 23–29 |
| Silicon dioxide | 5–8 |

All the agents were co-dissolved in tert-butanol (2-methyl-2-propanol) and the solution was freeze-dried for 20 hours by lyophilization. The weight ratio of phospholipids to total lipids was about 0.33:1 to 0.35:1. A dry CoQ10-lipid powder quickly dispersible in an aqueous medium was obtained.

Example 3

Preparation of Dry CoQ10-Lipid Mixture by a Double Freeze-Drying Process

This example illustrates the preparation of a dry CoQ10-lipid mixture of the composition described in Example 2 by a double freeze-drying process. All the agents were first co-dissolved in tert-butanol and the solution was freeze-dried for 20 hours by lyophilization. The dry CoQ10-lipid powder was then hydrated with water by mechanical shaking using a multiwrist shaker (LabLine) until the entire mixture was homogeneously dispersed in the aqueous phase. The dispersion was then homogenized for 5 minutes at 17,000 rpm using a Polytron PT 3000 (Kinematica, AG). The preparation was then submitted to high pressure homogenization using a Microlab 70 Gaulin or EMULSIFLEX™ homogenizer.

To the resultant dry CoQ10-lipid preparation, the cryoprotectant, sucrose (from a 40% w/w water solution), and the free-flowing imparting agent, CAB-O-SIL fumed silicon dioxide (from a 5% wlw solution in water), were added and the formulation was then freeze-dried using a Christ lyophilizer (Germany). The final dry CoQ10-lipid powder was filled into hard gelatin capsules.

Example 4

Preparation of Dry CoQ10-Lipid Mixture by Direct Spray-Drying

A dry CoQ10-lipid mixture of the same composition as in Example 1 was prepared by direct dissolution of all the agents in a ethanol:water 1:1 solution and spray-drying the mixture using a Yamato Pulvis GA32 Mini spray-dryer. The drying conditions were: flow rate 7 ml/min, inlet temperature 130° C., outlet temperature 80° C., and drying air flow 0.45 m$^3$/min. A homogeneous dry powder containing the CoQ10-lipid mixture was obtained.

Example 5

Preparation of Dry CoQ10-Lipid Mixture by high Pressure Homogenization of a Aqueous Dispersion Followed by Spray-Drying This example illustrates the preparation of a dry CoQ10-lipid mixture of the composition described in Example 1 by dispersing all the agents in an aqueous solution containing 10% ethanol using a Polytron PT 3000 (Kinematica, AG) (5 minutes at 17,000 rpm). The preparation was then submitted to high pressure homogenization using a Microlab 70 Gaulin or EMULSIFLEX™ homogenizer.

The resultant formulation was spray-dried using a Yamato Pulvis GA32 Mini spray-dryer. The drying conditions were: flow rate 7 ml/min, inlet temperature 150° C., outlet temperature 75° C., and drying air flow 0.5 m$^3$/min. A homogeneous dry powder containing the CoQ10-lipid mixture was obtained.

Example 6

In Vitro Release of CoQ10 from CoQ10-Dry Lipid Mixtures

FIG. 1 shows the in vitro release patterns of CoQ10 from a dry CoQ10-lipid mixture formulation and the commercial product ENERGYCO® CoQ10 (Herbamed-Assutech Ltd., Rehovot, Israel) in simulated gastric fluid.

In vitro drug release of CoQ10 from a dry CoQ10-lipid mixture formulation and from a commercial product containing equivalent amounts of CoQ10 were determined by placing a hard gelatin capsule in 50 ml of simulated gastric fluid (150 mM NaCl, pH 1.2, 37° C.) containing 1% Tween 80 as sink. Gentle stirring was provided by a magnetic bar. Samples were drawn from the release medium at prefixed time intervals, filtered through a 2.7 μm Whatman GF filter and analyzed for CoQ10 concentration using the UV method above described.

The amount of CoQ10 released was determined in the commercial product, dry lipid mixture formulation, and release medium studied by extraction with Dole reagent (isopropanol:heptane:water, 45:36:17) and measuring absorbance at 270 nm using a calibration curve. CoQ10 samples (0.5 ml) were added to 3.5 ml of Dole reagent and mixed thoroughly and the two phases were allowed to separate for 10 min at room temperature. CoQ10 was extracted selectively in the heptane upper phase of the Dole reagent and subsequently transferred to a quartz cuvette for absorbance measurement.

The % release of CoQ10 from the marketed product was very low compared to a very significant release (50% after 2 hours) from the dry lipid mixture formulation of Example 1. Each ENERGYCO® CoQ10 hard gelatin capsule contains 50 mg of CoQ10 mixed with rice powder. After capsule disruption in the simulated gastric fluid, big aggregates or clusters of CoQ10 and swelled rice powder were observed. These observations may explain the low CoQ10 dissolution into the release medium. Since particle size is a determinant factor in the rate and extent of drug absorption from the gastrointestinal tract, this result indicates low oral bioavailability of CoQ10 from the commercial product. These properties should be contrasted with those of the dry lipid mixture formulation of the present invention, which is quickly dispersible in the simulated gastric fluid.

Example 7

Human Oral Bioavailability of CoQ10 After Administration of CoQ10-Dry Lipid Mixtures Packed in Hard Gelatin Capsules

Figure 2:
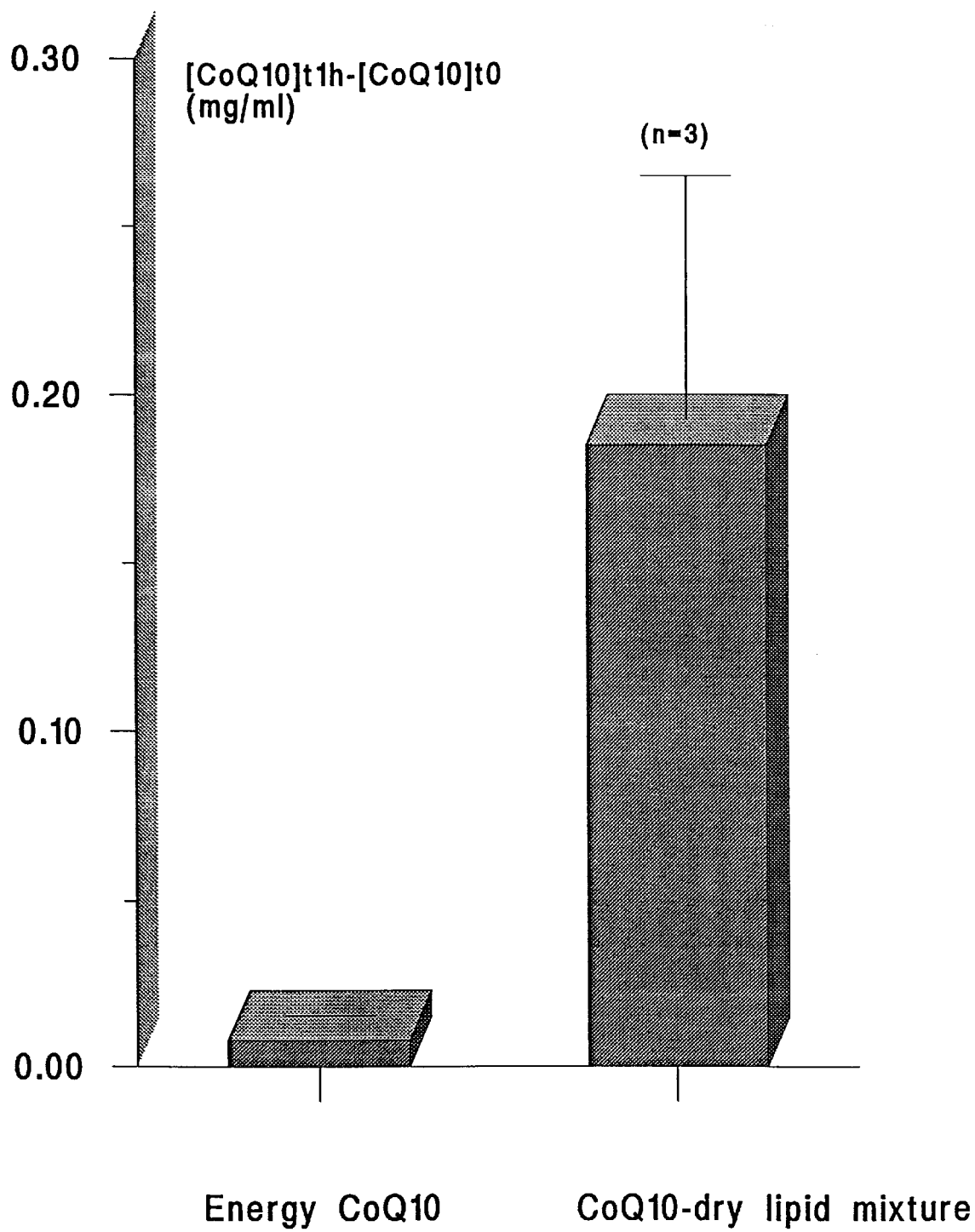
FIG. 2 shows the CoQ10 human plasma levels after oral administration of ENERGYCO® CoQ10 gelatin capsules and a CoQ20-dry lipid mixture prepared as described in Example 5 and packed in gelatin capsules.

The results of a human oral bioavailability study involving oral ingestion of a 50 mg hard gelatin capsule containing the free CoQ10 product and CoQ10-dry lipid mixtures formulation are presented in FIG. 2.

Hard gelatin capsules containing CoQ10 either as the free compound (ENERGYCO® CoQ10, Herbamed-Assutech Ltd., Rehovot Israel) or as a dry lipid mixture formulation were administered orally to human volunteers. Plasma samples for CoQ10 analysis were drawn before and 1 h post administration.

CoQ10 in plasma samples was identified and quantified by HPLC (Grossi G., Bargossi A. M., Fiorella P. L., and Piazzi S., Improved HPLC method for the determination of coenzyme Q10 in plasma, J. Chromat., 593, 217–226, 1992). Blood samples were drawn into plastic test tubes containing EDTA. Plasma was separated by centrifugation in a non-cooled centrifuge and stored at −20° C. until analyzed. COQ10 was extracted from plasma with hexane. After evaporation to dryness, samples were dissolved in isopropanol for HPLC. The mobile phase consisted of methanol:isopropanol (4:1). Detection was carried out by a UV detector at 275 nm wavelength.

Enhanced CoQ10 plasma levels 1 h post administration were observed with the dry lipid mixture-CoQ10 formulation of Example 1 compared to very low plasma concentration for the commercial COQ10 product supporting the in vitro release results. The results of this experiment are presented in FIG. 2.

Example 8

Preparation of Powdered Dexanabinol-Lipid Mixtures by Direct Spray-Drying

This example illustrates the preparation of powdered Dexanabinol-lipid mixtures of the composition described in Table 3 and prepared by direct spray-drying.

TABLE 3

Composition of powdered Dexanabinol-lipid mixtures prepared by direct spray-drying.

| | Agents | | |
|---|---|---|---|
| | AY-122-62-01 (% w/w) | AY-122-62-2 (% w/w) | AY-122-62-3 (% w/w) |
| Dexanabinol | 12.0 | 20.0 | 30.0 |
| Tricaprin | 34.0 | 34.0 | 34.0 |
| Lecithin | 17.0 | 17.0 | 17.0 |
| Tocopherol succinate | 0.4 | 0.4 | 0.4 |
| Silicon dioxide | 36.6 | 36.6 | 36.6 |

All lipid components were dissolved in ethanol. Cab-O-sil was added from a 5% water dispersion to the ethanolic solution (at a final ethanol:water, v/v ratio of 2:1) and the mixture was shaken at 40° C. for several minutes. The mixture was then spray-dried using a Yamato Pulvis GA32 Mini spray-dryer. The drying conditions were: flow rate 7 ml/min, inlet temperature 130° C., outlet temperature 80° C., and drying air flow 0.45 m$^3$/min. The weight ratio of phospholipids to total lipids was 0.33:1. Homogeneous dry quick-dispersible powders containing the Dexanabinol-lipid mixture were obtained.

Example 9

In vitro Release of Dexanabinol from Powdered Dry Lipid Compositions

In vitro drug release of Dexanabinol from powdered dry lipid compositions was determined by placing a hard gelatin capsule No. 1 containing the formulation in 50 ml of simulated gastric fluid (150 mM NaCl, pH 1.2, 37° C., containing 1% Tween 80 as sink). Gentle stirring was provided by a magnetic bar. Samples were drawn from the release medium at prefixed time intervals and filtered through a 2.7 $\mu$m PTFE filter (Whatman).

Dexanabinol was determined by HPLC using a Kontron instrument equipped with pump, UV detector, and autosampler. A summary of the typical chromatographic conditions of the method is provided below:
Column: Merck 50980 supersphere 100 RP-18, 75×4 mm, 4 $\mu$m. Mobile Phase: 30% phosphate buffer (0.01 M KH$_2$PO$_4$, pH 3.0): 70% acetonitrile (v/v). Flow rate: 1 ml/min. Detector wavelength: 280 nm. Injection volume: 20 $\mu$l. Column temperature: ambient. Retention time: about 5.8 min. Run time: about 9 min.

Figure 3:
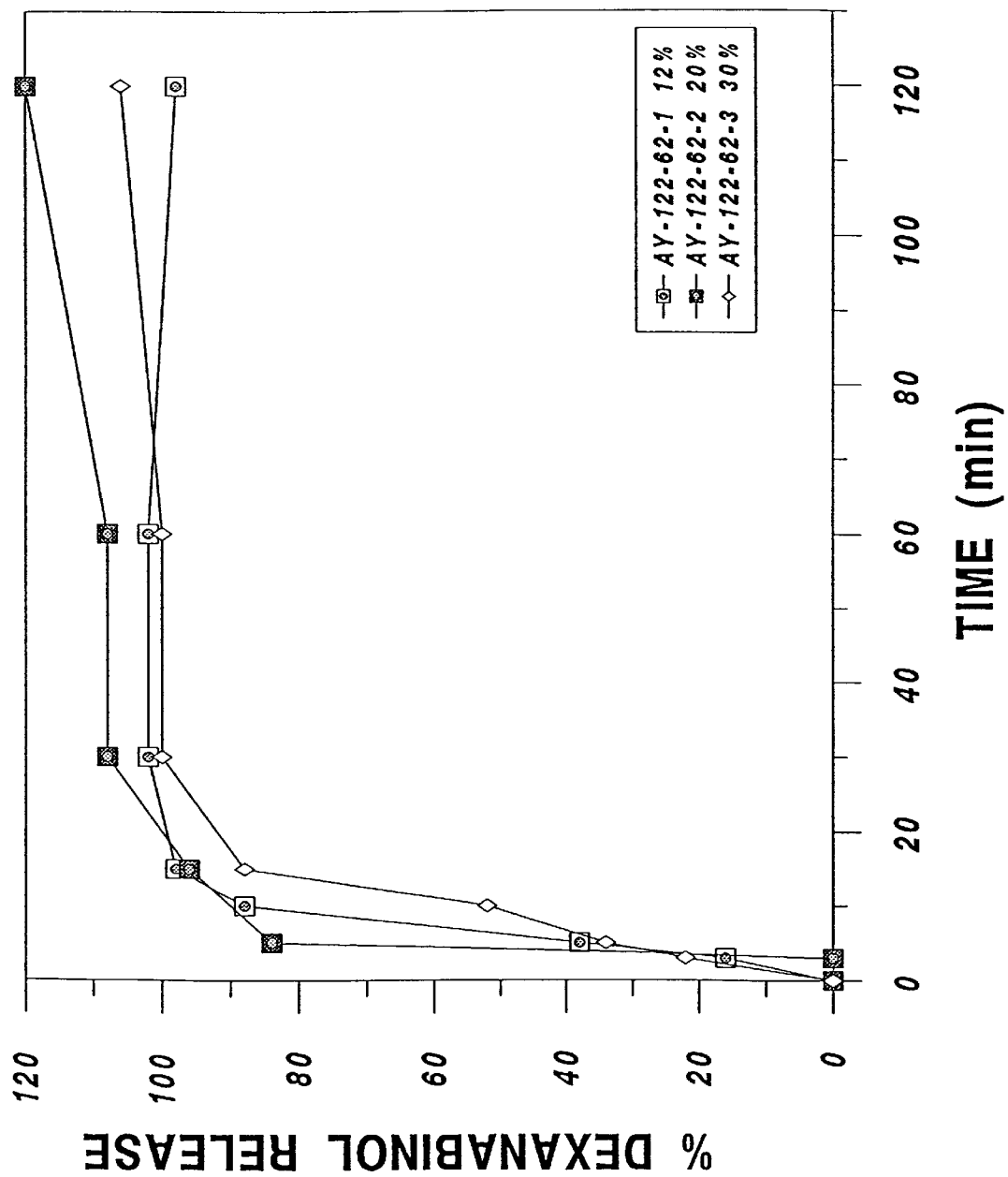
FIG. 3 shows the in vitro release patterns of Dexanabinol in simulated gastric fluid from powdered dry lipid compositions (Formulations AY-122-62-1, AY-122-62-2, AY-122-62-3) prepared as described in Example 8 (Table 3) and packed in hard gelatin capsules.

FIG. 3 shows the in vitro release patterns of Dexanabinol in simulated gastric fluid from powdered dry lipid compositions (Formulations AY-122-62-1, AY-122-62-2, AY-122-62-3) prepared as described in Example 8 (Table 3) and packed in hard gelatin capsules. The three formulations tested differed in the weight % of Dexanabinol from 12 to 30% of drug per total solids. Very quick Dexanabinol release patterns from 80–100% were obtained during the initial 10–20 min.

Example 10

Rat Oral Bioavailability of Dexanabinol After Administration of a Powdered Dry Lipid Composition Packed in Hard Gelatin Minicapsules

The Dexanabinol dry-lipid mixture was filled in hard gelatin minicapsules (Torpac, N.J., USA) and tested for oral bioavailability studies in rats. Male Sprague-Dawley rats (220–260 g, n=7) were administered orally with the Dexanabinol formulation at a 30 mg/kg dose. Blood samples were collected at 0,0.5, 1.0, 2.0,3.0, 5.0,8.0, and 24 hours time intervals. The samples were centrifuged at 10,000 rpm for 5 min and the plasma was separated and stored frozen at −20° C. until plasma Dexanabinol levels were analyzed. Determination of Dexanabinol in plasma was performed by HPLC. The chromatographic conditions were as described in Example 3. Plasma samples stored at −20° C. were defrosted and diluted 1:4 as follows: 150 $\mu$l plasma sample was transferred into a 1.8 ml Eppendorf tube and 150 $\mu$l of acetonitrile was added. The sample was vortexed and centrifuged in a microfuge for 10 minutes at 10,000 rpm. The upper clear liquid transferred into HPLC glass conical vial. A calibration curve was used for calculating Dexanabinol plasma levels. Corrections of sample peak areas were done by subtracting the average value of the peak area obtained for samples at zero time (blank plasma).

Figure 4:
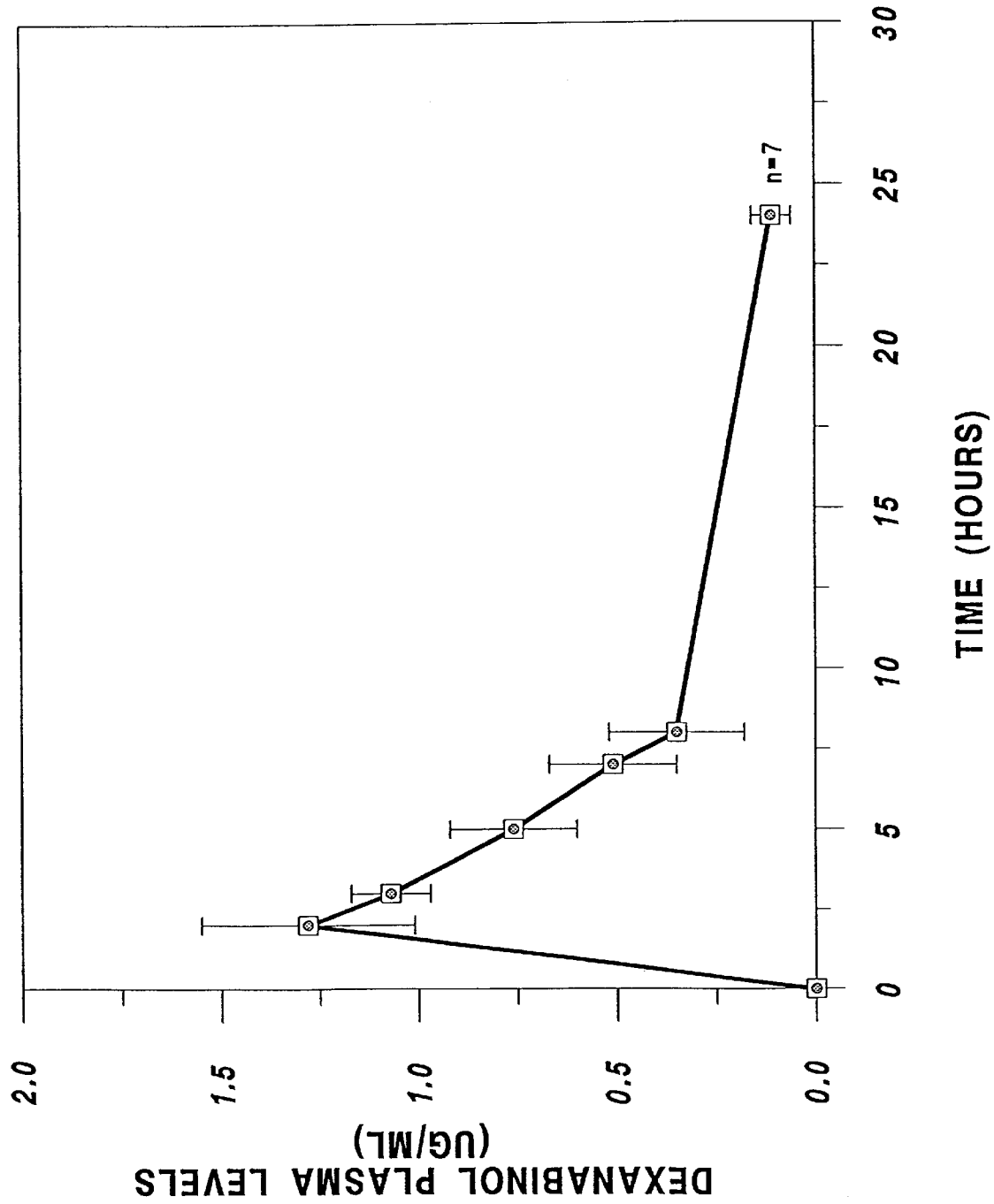
FIG. 4 shows the Dexanabinol rat plasma levels after oral administration (30 mg/kg drug, n=7) of a powdered dry lipid composition (Formulation AY-122-62-3) prepared as described in Example 8 (Table 3).

FIG. 4 shows the oral pharmacokinetics of Dexanabinol rat plasma levels after administrating to rats (30 mg/kg drug, n=7) the powdered dry lipid composition (Formulation AY-122-62-3) prepared as described in Example 8 (Table 3).

Very significant Dexanabinol plasma levels were obtained demonstrating enhanced oral absorption of Dexanabinol from the drug-lipid mixture formulation and indicating the good water dispersibility of the formulation. These properties probably facilitate the uptake of the drug from the gastrointestinal tract. A maximal drug concentration ($C_{max}$) of about 1.3 mg/ml was obtained after 2 hours ($t_{max}$).

Example 11

Solid Lipid Mixture of CoQ10 in the Form of a Water-Dispersible Powder Quickly Reconstituted as Drinkable Product or Beverage A beverage product containing Coenzyme Q10 is provided which can conveniently be used for human consumption. An ideal water-based CoQ10 beverage should contain this supplement substantially homogeneously dispersed, suspended or dissolved in the aqueous medium to allow CoQ10 to be absorbed efficiently through the gastrointestinal tract and show its beneficial properties. The solid lipid compositions described herein were also examined for their suitability for the preparation of a CoQ10 beverage product in the form of a powdered dry lipid mixture packed in a sachet to be reconstituted in water, or any other aqueous medium.

To be acceptable in a beverage, the CoQ10 lipid mixture formulation has to be optimized to be a quickly water-dispersible powder. To achieve this goal, a fine and free-flowing powdery material with a small range of particle size distribution has to be obtained. This conclusion was reached as a result of a series of experiments which investigated the chemical and physical stability of the mixture when treated with various surface active materials and emulsifiers.

Formulations containing the water-reconstitutable powdery dry solid lipid mixtures or solid lipid compositions of CoQ10 and different surface active agents were also prepared by direct spray-dry or freeze-dry according to the methods described in Examples 1 to 5. Several representative surface active agents were tested using solid lipid mixtures of CoQ10 according to the following list:

| Surfactant | Example | Amount (w/w %) |
| --- | --- | --- |
| Polysorbate | Tween 60 | 0.1–10% |
| Sorbitan stearate | Span 80 | 0.1–10% |
| Glycerides | Myverol, Myvatex | 0.1–10% |

The CoQ10-lipid compositions containing the surfactants were mixed with water and quickly formed dispersible aqueous suspensions. Such Coenzyme Q10 solid lipid compositions may more preferably be dispersed in a palatable fluid or beverage such as a fresh or packaged fruit juice or any other commercially available beverage.

The surfactant compounds can be added either directly added to the initial composition of the solid lipid mixtures, or to the aqueous medium to be used as fluid for final reconstitution of the dry powder. In addition to the materials listed above, other synthetic surface active materials or emulsifiers which are known in the art can be added to the dispersion prior to drying to assist in the resuspension of the composition in a liquid medium. The amount of these materials would typically be in the range of between about 0.1 and 15% by weight. These dry CoQ10-lipid mixtures may also contain other additive excipient materials of the types that are typically used in food products, such as sugars, preservatives, coloring agents and flavors. One of ordinary skill in the art would be aware of the specific types and concentrations of such materials that are commonly used.

What is claimed is:

1. A dry solid lipidic composition comprising: a first component of a lipophilic substance selected from the group consisting of a cannabinoid, steroid, a steroid antagonist, a non-steroidal antiinflammatory agent, an antifungal agent, an antibacterial agent, an antihypertensive agent, an antioxidant, an anti-epileptic agent, an antiviral agent, an anticancer agent, and an antidepressant in an amount of about 0.01 to 50% by weight of the lipidic composition to provide a therapeutic effect when administered to a mammal; a second component comprising at least one fat which is a solid at about 25° C. and which is present in an amount of about 20 to 75% of the weight of the lipidic composition; and a third component of at least one phospholipid which is present in an amount of about 2 to 40% by weight of the lipidic composition, with these three components totaling 100% of the lipidic composition, wherein the second and third components increase the oral availability of the lipophilic substance when administered to the mammal.

2. The composition of claim 1 wherein the fat is a triglyceride a mixture of tirglycerides.

3. The composition of claim 1 wherein the phospholipid is a lecithin.

4. The composition of claim 1 wherein the weight ratio of phospholipid to total of phospholipid and solid fat is about 0.1:1 to 2:1.

5. The composition of claim 1 further comprising a solid carrier in the amount of about 5–50% of the total weight of the composition.

6. The composition of claim 1 wherein the composition is present in a dosage form selected from the group consisting of a gelatin capsule, a tablet, and a beverage comprising a suspension of the composition.

7. A method for producing the dry solid lipid composition of claim 1 which comprises:

dissolving the three components in a suitable organic solvent; and drying the dispersion to form the dry solid lipid composition.

8. A method for producing the dry solid lipid composition of claim 1 which comprises:

dissolving the three components in a suitable organic solvent;

evaporating the solvent to complete dryness;

hydrating the resulting dry solid lipid composition with an aqueous phase to obtain a lipid dispersion in water;

homogenizing the resultant lipid dispersion to reduce the particle size to the submicron range; and drying the homogenized dispersion to form the dry solid lipid composition.

9. The method of claim 7 wherein the drying is achieved by spray drying or freeze drying the dispersion.

10. The method of claim 7 which further comprises adding a cryoprotectant or solid diluent to the dispersion prior to drying.

11. The method of claim 7 which further comprises adding a synthetic surface active material or an emulsifier to the dispersion prior to drying to assist in the resuspension of the composition in a liquid medium.

12. A method for delivering a lipophilic substance to a mammal in need of such substance which comprises orally administering a therapeutically effective amount of the composition of claim 1.

13. The method of claim 8 wherein the drying is achieved by spray drying or freeze drying the dispersion.

14. The method of claim 8 which further comprises adding a cryoprotectant or solid diluent to the dispersion prior to drying.

15. The method of claim 8 which further comprises adding a synthetic surface active material or an emulsifier to the dispersion prior to drying to assist in the resuspension of the composition in a liquid medium.

16. The composition of claim 1 wherein the lipophilic substance is Coenzyme Q10.

17. The composition of claim 1 wherein the lipophilic substance is dexanabinol.

18. The composition of claim 16 further comprising at least one of a peroxide, α-tocopherol, tocopherol succinate, or butylated hydroxytoluene.

19. The composition of claim 1 further comprising at least one of an amino compound, a polysaccharide, a cyclodextrin, or polyvinylpyrrolidone.

20. The composition of claim 5 wherein the solid carrier is silicon dioxide, starch, lactose, sucrose, sorbitol, talc, stearic acid, magnesium stearate, or dicalcium phosphate.

* * * * *